(12) United States Patent
Doerflinger

(10) Patent No.: US 10,818,396 B2
(45) Date of Patent: Oct. 27, 2020

(54) METHOD AND SYSTEM FOR NATURAL LANGUAGE PROCESSING FOR THE EVALUATION OF PATHOLOGICAL NEUROLOGICAL STATES

(71) Applicant: Jane Doerflinger, Summit, NJ (US)

(72) Inventor: Jane Doerflinger, Summit, NJ (US)

( * ) Notice: Subject to any disclaimer, the term of this patent is extended or adjusted under 35 U.S.C. 154(b) by 0 days.

(21) Appl. No.: 15/836,847

(22) Filed: Dec. 9, 2017

(65) Prior Publication Data

US 2019/0180871 A1 Jun. 13, 2019

(51) Int. Cl.
| | |
|---|---|
| *G10L 17/26* | (2013.01) |
| *G16H 50/20* | (2018.01) |
| *G10L 15/18* | (2013.01) |
| *G06F 40/20* | (2020.01) |
| *G06F 40/30* | (2020.01) |
| *G06F 7/02* | (2006.01) |

(52) U.S. Cl.
CPC ............. *G16H 50/20* (2018.01); *G06F 40/20* (2020.01); *G06F 40/30* (2020.01); *G10L 15/1815* (2013.01); *G06F 7/02* (2013.01); *G10L 17/26* (2013.01)

(58) Field of Classification Search
CPC ....................................................... G10L 17/26
See application file for complete search history.

(56) References Cited

U.S. PATENT DOCUMENTS

| | | | |
|---|---|---|---|
| 6,622,140 B1 * | 9/2003 | Kantrowitz | .............. G06K 9/62 |
| 9,619,613 B2 | 4/2017 | Meyer et al. | |
| 9,685,174 B2 | 6/2017 | Karam | |
| 2002/0194002 A1 * | 12/2002 | Petrushin | ................ G10L 17/26 |
| | | | 704/270 |
| 2003/0069748 A1 * | 4/2003 | Shear | ................. G06Q 30/0271 |
| | | | 705/67 |
| 2007/0124135 A1 * | 5/2007 | Schultz | ................... G10L 17/26 |
| | | | 704/201 |
| 2013/0166291 A1 * | 6/2013 | Lech | ....................... G10L 17/26 |
| | | | 704/232 |
| 2014/0091897 A1 * | 4/2014 | Lemmey | ................ A61B 5/165 |
| | | | 340/3.1 |
| 2016/0359697 A1 * | 12/2016 | Scheib | ................ H04L 43/0829 |
| 2017/0119302 A1 | 4/2017 | Clyde et al. | |

FOREIGN PATENT DOCUMENTS

| | | |
|---|---|---|
| EP | 2555675 | 2/2013 |
| WO | 2017068582 | 4/2017 |

* cited by examiner

*Primary Examiner* — Feng-Tzer Tzeng

(74) *Attorney, Agent, or Firm* — Andrew Morabito

(57) ABSTRACT

The invention relates to a method for determining and assisting an impairment in a patient's cognitive or emotional condition, the method comprising, receiving, by one or more computing devices, a first set of data from a patient, gathering, by one or more computing devices, a second set of data from a patients' computing device, analyzing, by one or more computing devices, a first portion of the first set of data with a pre-trained neural net, processing, by one or more computing devices, a second portion of the second set of data, calculating, by one or more computing devices, a value based on the analyzed first portion of the first set of data and the processed second portion of the second set of data.

22 Claims, 4 Drawing Sheets

METHOD AND SYSTEM FOR NATURAL LANGUAGE PROCESSING FOR THE EVALUATION OF PATHOLOGICAL NEUROLOGICAL STATES

BACKGROUND

This disclosure relates generally to mental and emotional assistance, and more specifically to a method, computer program and computer system for efficiently detecting when a patient is having an episode, experiencing neurological symptoms, or recovering from a condition and providing adequate and instantaneous support.

One of the major problems in today's psychiatry common practice is the follow-up on patients; it is difficult to achieve fluent monitoring on a patient's condition. The result is low adherence to the treatment, neglecting medication or psychotherapy or both. While experiencing acute symptoms, patients are even more likely to change dosage without consulting their therapists. And when their condition improves, they may not recognize their medication as a preventive measure, and stop taking it. Low adherence rates for drugs or other treatments can lead to worse, more frequent episodes, which may decrease their functioning between episodes as well. Many times, patients do not seek treatment again until the next episode is disabling to the full extent, and requires major intervention. Additionally, many patients who are compliant still require additional monitoring, because their symptoms are unpredictable Currently, maintaining follow-up on a patient is based mainly on face to face contact, but may also include short telephone conversations or emails. This kind of connection is limited and doesn't allow bidirectional flow of information in a fluent manner. The therapist (the psychiatrist, psychologist or any other mental health professional) is unable to really monitor the patient's condition between appointments. Psychiatrists, therapists and physicians cannot properly monitor drug adherence or assignments, such as those given in cognitive behavioral therapies, which are the key to the therapy's success. The therapist is also unaware of the patient's clinical condition, e.g., general mood, sleep quality, etc. Lack of regular monitoring on a mental health patient leads directly to more hospitalizations, disability and frequent visits, since the only way today to retrieve a mental health patient's clinical measures is by direct interview.

Therefore, there is desire for a system or program that allows continuous communication between the providers and the client so that the provider can properly monitor the client and the client has a means to help determine if and when an episode may be occurring, and further assisting the provider with a plurality of information they would generally not be privy to.

SUMMARY

A first aspect of the present invention provides a method for identifying, measuring the severity of, and providing care for an impairment in a patient's cognitive or emotional condition, the method comprising; receiving, by one or more computing devices, a first set of data from a patient, gathering, by one or more computing devices, a second set of data from a patients' computing device, analyzing, by one or more computing devices, a first portion of the first set of data with a pre-trained neural net, plotting, by one or more computing devices, the first portion of the first set of data in a predetermined graphical representation of at least one language, processing, by one or more computing devices, a second portion of the second set of data, and calculating, by one or more computing devices, a value based on the analyzed first portion of the first set of data and the processed second portion of the second set of data.

A second aspect of the present invention provides a computer program product for identifying, measuring the severity of, and providing care for an impairment in a patient's cognitive or emotional condition, the computer program product comprising: one or more computer readable storage media and program instructions stored on the one or more computer readable storage media, the program instructions comprising; program instructions to receive a first set of data from a patient, program instructions to gather second set of data from a patients' computing device, program instructions to analyze a first portion of the first set of data with a pre-trained neural net, program instructions to plot the first portion of the first set of data in a predetermined graphical representation of at least one language, program instructions to process a second portion of the second set of data, and program instructions to calculate a value based on the analyzed first portion of the first set of data and the processed second portion of the second set of data.

A third aspect of the present invention provides a computer system for protecting a resource, the computer program product comprising; one or more computer processors, one or more computer readable storage media, and program instructions stored on the one or more computer readable storage media for execution by, at least one of the one or more processors, the program instructions comprising; program instructions to receive a first set of data from a patient, program instructions to gather second set of data from a patients' computing device, program instructions to analyze a first portion of the first set of data with a pre-trained neural net, program instructions to plot the first portion of the first set of data in a predetermined graphical representation of at least one language, program instructions to process a second portion of the second set of data, and program instructions to calculate a value based on the analyzed first portion of the first set of data and the processed second portion of the second set of data.

DETAILED DESCRIPTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects may generally be referred to herein as a "circuit," "module", or "system." Furthermore, aspects of the present invention may take the form of a computer program product embodied in one or more computer readable medium(s) having computer readable program code/instructions embodied thereon.

Embodiments of the present invention discloses an approach to assist clients with their conditions in a safe and secure manner while also providing their providers with ample information to further assist the client to improve their condition and learn signals to help reduce the negative effects their conditions can inflict on them.

The severity of many neurological conditions varies unpredictably, making it hard for providers to track patients' health or offer as-needed care. For example, if a patient has bipolar disorder, they may experience manic episodes characterized by impulsivity, grandiosity, inability to sleep, speaking quickly, excessive spending, crime, and other signs and symptoms. If a patient has a psychotic disorder, they may experience periods of new or heightened psychotic symptoms, including delusions, inability to speak or think clearly, and paranoia. Many seniors experience cognitive decline, showing symptoms such as memory loss, motor problems, confusion, and inability to find words that appear and worsen unpredictably. In yet another example, brain damage patients often exhibit characteristics such as limited motor skills and language comprehension problems, which will hopefully respond to treatment. This invention allows these people—who often lack insight—to learn that they are having issues (or successful recovery!) so they can properly and safely address their conditions. The present invention will now be described in detail with reference to the Figures.

Figure 1:
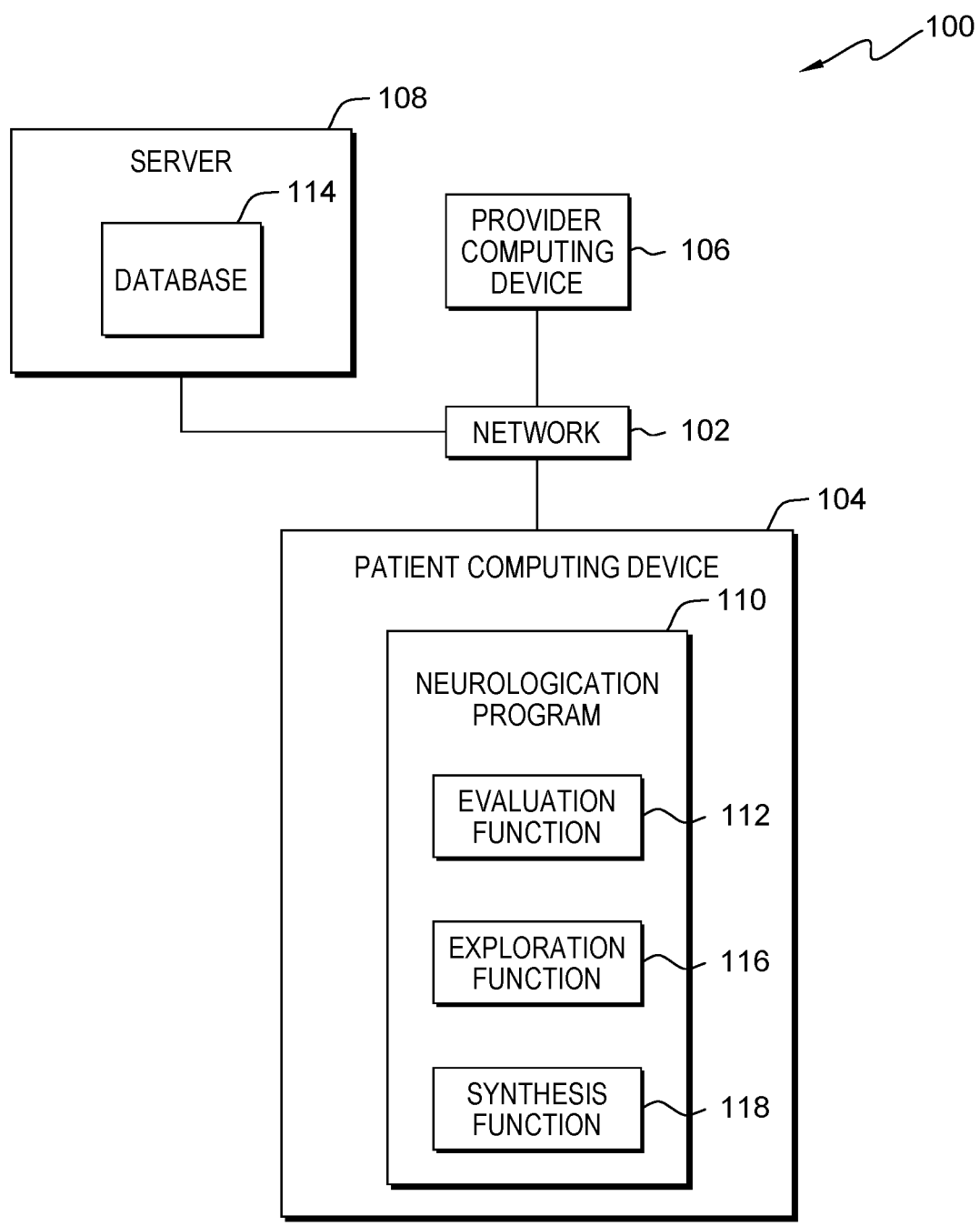
FIG. 1 depicts a block diagram depicting a computing environment, in accordance with one embodiment of the present invention.

FIG. 1 depicts a block diagram of a computing environment 100 in accordance with one embodiment of the present invention. FIG. 1 provides an illustration of one embodiment and does not imply any limitations regarding the environment in which different embodiments maybe implemented.

In the depicted embodiment, computing environment 100 includes network 102, patient computing device 104, provider computing device 106, server 108, Neurological program 110, evaluation function 112, exploration function 116, synthesis function 118 and database 114. Computing environment 100 may include additional servers, computers, or other devices not shown.

Network 102 may be a local area network (LAN), a wide area network (WAN) such as the Internet, any combination thereof, or any combination of connections and protocols that can support communications between patient computing device 104, provider computing device 106, and server 108 in accordance with embodiments of the invention. Network 102 may include wired, wireless, or fiber optic connections.

Patient computing device 104 may be a management server, a web server, or any other electronic device or computing system capable of processing program instructions and receiving and sending data. In some embodiments, patient computing device 104 may be a laptop computer, tablet computer, netbook computer, personal computer (PC), a desktop computer, or any programmable electronic device capable of communicating with provider computing device 106 and server 108 via network 102. In other embodiments, patient computing device 104 may represent a server computing system utilizing multiple computers as a server system, such as in a cloud computing environment. In another embodiment, patient computing device 104 represents a computing system utilizing clustered computers and components to act as a single pool of seamless resources. In the depicted embodiment, patient computing device 104 includes Neurological program 110, evaluation function 112, exploration function 116, synthesis function 118 and database 114. In other embodiments, patient computing device 104 may include any combination of Neurological program 110, evaluation function 112, exploration function 116, synthesis function 118 and database 114. Patient computing device 104 may include components, as depicted and described in further detail with respect to FIG. 5.

Provider computing device 106 may be a management server, a web server, or any other electronic device or computing system capable of processing program instructions and receiving and sending data. In other embodiments, provider computing device 106 may be a laptop computer, tablet computer, netbook computer, personal computer (PC), a desktop computer, or any programmable electronic device capable of communicating with patient computing device 104 via network 102. In other embodiments, provider computing device 106 may be a server computing system utilizing multiple computers as a server system, such as in a cloud computing environment. In one embodiment, provider computing device 106 represents a computing system utilizing clustered computers and components to act as a single pool of seamless resources. Provider computing device 106 may include components, as depicted and described in further detail with respect to FIG. 3.

Server 108 may be a management server, a web server, or any other electronic device or computing system capable of processing program instructions and receiving and sending data. In another embodiments server 108 may be a laptop computer, tablet computer, netbook computer, personal computer (PC), a desktop computer, or any programmable electronic device capable of communicating via network 102. In one embodiment, server 108 may be a server computing system utilizing multiple computers as a server system, such as in a cloud computing environment. In one embodiment, server 108 represents a computing system utilizing clustered computers and components to act as a single pool of seamless resources. In the depicted embodiment database 114 is located on server 108. Server 108 may include components, as depicted and described in further detail with respect to FIG. 3.

Neurological program 110 operates to perform an analysis of the patient's inputs to assist in determining if they are having an episode or relapse of their health issue(s). In one embodiment, the Neurological program 110 uses cognitive computing along with natural language processing and generates a score based on the patient's status. In the depicted embodiment, Neurological program 110 utilizes network 102 to access the provider computing device 106 and the server 108, and communicates with database 114. In one embodiment, Neurological program 110 resides on patient computing device 104. In other embodiments, Neurological program 110 may be located on another server or computing device, provided Neurological program 110 has access to database 114, evaluation function 112, exploration function 116, and synthesis function 118.

Evaluation function 112 operates to receive, process, analyze, score, and communicate with the patient and additional personnel, and assists the patient in determining if additional services are required and if the patient is improving or having an episode. In the depicted embodiment, evaluation function 112 is part of Neurological program 110 located on the patient computing device 104. In other embodiments, evaluation function 112 may be a stand-alone program located on another server, computing device, or program, provided evaluation function 112, exploration function 116, synthesis function 118, Neurological program 110, and database 114 are able to communicate with one another.

Exploration function 116 operates to process the data that is supplied by the patient through the patient computing device 104 to determine the situation of the patient based on the processing of the data. In the depicted embodiment, exploration function 116 is part of Neurological program 110 located on the patient computing device 104. In other embodiments, exploration function 116 may be a stand-alone program located on another server, computing device, or program, provided exploration function 116, evaluation function 112, synthesis function 118, Neurological program 110, and database 114 are able to communicate with one another.

Synthesis function 118 processes the supplied data and data that is received by the patient computing device 104 to further assist in determining if the patient is having an episode. The synthesis function 118 uses the processed data from the exploration function 116 and the data gathered from the evaluation function 112. In the depicted embodiment, synthesis function 118 is part of Neurological program 110 located on the patient computing device 104. In other embodiments, synthesis function 118 may be a stand-alone program located on another server, computing device, or program, provided synthesis function 118, evaluation function 112, exploration function 116, Neurological program 110, and database 114 are able to communicate with one another.

Database 114 may be a repository that may be written to and/or read by Neurological program 110, evaluation function 112, exploration function 116, and synthesis function 118. Information gathered from structured data source 110 and/or unstructured data source 112 may be stored to database 114. Such information may include previous scores, audio files, textual breakdowns, facts, events, and contact information. In one embodiment, database 114 is a database management system (DBMS) used to allow the definition, creation, querying, update, and administration of a database(s). In the depicted embodiment, database 114 resides on patient computing device 104. In other embodiments, database 114 resides on another server, or another computing device, provided that database 114 is accessible to Neurological program 110 and evaluation function 112, exploration function 116, and synthesis function 118.

Figure 2:
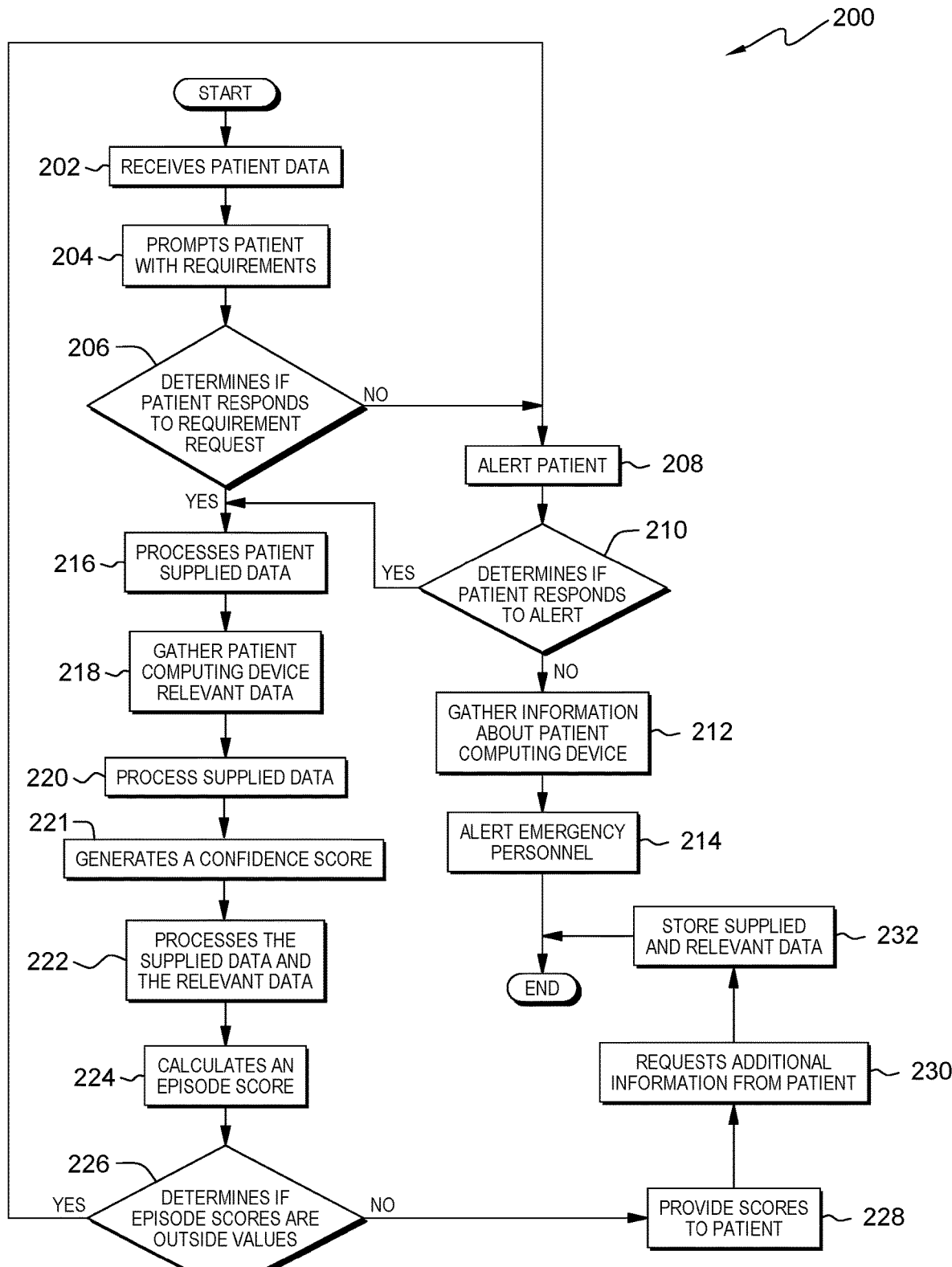
FIG. 2 depicts a flowchart of the operational steps taken by neurological program to determine if a patient is having an episode with the assistance of a computing device within the computing environment of FIG. 1, in accordance with an embodiment of the present invention.

FIG. 2 shows flowchart 200 depicting a method according to the present invention. The method(s) and associated process(es) are now discussed, over the course of the following paragraphs, with extensive reference to FIG. 2, in accordance with one embodiment of the present invention.

The program(s) described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The Neurological program 110 is used to assist providers who evaluate neurological states such as psychosis, cognitive impairment, mania, and the like. This type of evaluation information is increasing more expensive and widely unavailable in large parts of the country. The task often falls to family members, who are ill-equipped to recognize and respond to a problem. Patients try to monitor themselves, but often experience a lack of insight as a symptom of their condition. Insufficient evaluation leads to distress, greater life disruption (such as unemployment and imprisonment), and according to many psychologists, worse long-term outcomes. If a person's mental state could be automatically tested using a smartphone, it would mean more frequent and less expensive monitoring which would lead to better care for patients and a greater ability to live independently.

Experts can detect and evaluate a neurological disturbance after conversing with a patient for only a few seconds. Technology has advanced to the point where algorithms can detect the same cues to evaluate a patient's symptoms of neurological conditions including psychosis, mania, brain damage (caused by stroke or head trauma), Alzheimer's, and dementia. The Neurological program 110 prompts patients to speak ("Tell me what you did today." "Please describe this picture" etc.) and records patients' answers. The voice recording is analyzed, reports the patient's health, automatically messages an emergency contact, and saves the results to a record of the patient's symptoms. This could be used by prediagnosed patients to monitor their own health, by general care doctors to identify patients who may be on the brink or the middle of a mental health crisis, and by professionals who work with populations where neurological disorders are common (such as nursing homes, homeless shelters, prisons, and the military).

The Neurological program 110 evaluations will be inexpensive and administrable by non-experts. It offers numerical scores of patient's health, rather than subjective judgments, which are easier to compare to one another and may be helpful to patients who lack insight into their conditions or who have impaired social skills. Because it can be deployed at any time, it could be particularly helpful for people who experience psychosis, which requires immediate emergency treatment to optimize long-term outcomes. And it provides patients' an objective record of their symptoms, which can be easily transferred from one health care provider to another.

In step 202, evaluation function 112 receives patient data. These inputs may be input by the patient or a provider. This information may be, but not limited to, the type of mental or physical illness or condition of the patient, personal information about the patient, emergency contact information, medication, other providers information, or other information that is relevant and necessary for the provider and the patient to easily communicate information with one another, as well as with predetermined parties. In some embodiments, the inputs related to the global positioning the patient computing device 104. In some embodiments, this information is input on the patient computing device 104. In additional embodiments, it may be input on the provider computing device 106 or another device.

In step 204, evaluation function 112 prompts the patient to produce a predetermined quantity of requirements, such as of answers to prompts. These requirements are to establish a standard for the patient so that as the patient continues to use the Neurological program 110 or functions, the Neurological program 110 or the functions provides more accurate and correct results. These requirements, may be, but not limited to, processing the patient a predetermined number of times to establish various severities of their condition, to best understand the specific client's situation. In some embodiments, a standard is established without the need of the patient's initial requirements. The evaluation function 112 may require these requirements input with the supervision of a provider. The evaluation function 112 may require these requirements input within a predetermined time period of using the Neurological program 110 or the functions. The Neurological program 110 or the functions may periodically at either random or predetermined times, requested that the patient input the required information. The time between these prompts, may be, but limited to, may be set by the Neurological program 110, the provider, at random, or at a set predetermined time frame, or the like.

In decision 206, evaluation function 112 determines if the patient responds to requirement request. The patient is required to check in, or communicate with the Neurological program 110 or the functions within predetermined intervals. These intervals can be set at daily, weekly, monthly, etc. time frames. The Neurological program 110 or the functions also accounts for the patient's ability to personally check in additional times to the required minimum number of times. The check in process requires the patient to respond to a variety of audio request such as questions or commands to respond to. The requests, for example, may be questions that require an answer that is more than one word. In some embodiments, evaluation function 112 provides a predetermined time frame for the patient to check in within the intervals. For example, if the patient is supposed to check in each morning, there may be a tolerance to allow for checking in until noon that day. In additional embodiments, evaluation function 112 provides audio or physical notifications (e.g. vibrations or sounds) to the patient to alert them to the request to check in. If evaluation function 112 determines that the patient has checked in and responded to the requested prompts (YES branch, proceed to step 216) evaluation function 112 gathers the patient supplied data. If evaluation function 112 determines that the patient has not checked in and has not responded to the requested prompts (NO branch, proceed to step 208) evaluation function 112 alerts the patient. In some embodiments, the patient is not required to check in and this step is overridden by the patient's ability to check in at their discretion. In some embodiments, there may be additional personnel who are contacted that the alert has been sent to the patient, such as, but not limited to, their provider and predetermined people.

In some embodiments, evaluation function 112 prompts the patient with audible requests when checking in. These audible requests may have, stipulations associated with them, for example, asking the patient questions, such as, but not limited to "tell me about something that happened to you on your birthday" or "what did you do last weekend." The audible requests are designed to require the patient to respond with more than one-word answers. In some embodiments, the patient is required to speak for a predetermined set of time (e.g. 15 seconds, 30 seconds, etc.). This provides adequate data to assess in the later steps. The response by the patient may be based on requests that require an extended response to gather the necessary amount of audible information, such as, but not limited to, pauses, pitch of voice, speed of talking, choice of words (e.g. curse words), articulation of words.

If a video requirement is requested, the camera will need to capture a specific act of the patient or a prolonged exposure to the patient's face. This is designed to show that the patient is able to receive the request, process the request, and complete the request. If the patient's face is requested it is used to detect and analyze specific acts of the patient, such as, but not limited to, rapid eye movement, or the like.

In step 208, evaluation function 112 alerts the patient of their lack of checking in. This assists the patient in checking in to remove the alert status. In some embodiments, the alert may be audio, visual, physical, or a combination of these to direct the patient's attention to the program. An example of a physical alert, is the vibration of the computing device.

In decision 210, evaluation function 112 determines if the patient responds to the alert. This provides the patient the ability to personally remove the alert status. This can be for various reasons such as if the patient not having their phone, if they have been in a situation that does not allow access to their device, or if their device lost power. The patient has a predetermined time frame to respond to the alert. If evaluation function 112 determines that the patient has responded to the alert (YES branch, proceed to step 216) evaluation function 112 gathers the patient supplied data. If evaluation function 112 determines that the patient has not responded to the alert (NO branch, proceed to step 212) evaluation function 112 gather patient computing device information.

In step 212, evaluation function 112 gathers information about the patient computing device 104 to determine how to best advise the emergency personnel. In one embodiment, this is transmitting the last audio, visual, and messages or communications sent to best provide information that would be able to locate the patient computing device 104. In some embodiments, the alerting of the emergency personnel activates the global positioning system of the patient computing device 104 in an attempt to further increase the response time and location of the patient.

In step 214, evaluation function 112 alerts emergency personnel to the patient's lack of response or emergency situation. This assists with helping to protect the patient if they are having an episode. If a patient is not responding to the request it is likely they are having another episode and are in possibly in danger to themselves and others. The emergency personnel can be providers, family, medical providers, the police, or the like which are able to help the patient.

In step 216, evaluation function 112 process the response(s) supplied by the patient. The evaluation function 112 gathers the response(s) of the patient. This may include the audio, visual, time data (e.g. time of day, day of the week, etc.) and physical data (e.g. gyroscope, accelerometer, proximity sensors, and the like) gathered by the user computing device 106. For example, if the supplied data is audio, the function 112 records the length, volume, presence of sound, absence of sound pitches, intensity, loudness, doppler effect, the quality, and other characteristics of the supplied audio.

In step 218, evaluation function 112 gathers patient computing device 104 relevant data. This relevant data is additional data supplied by the Neurological program 110, the functions, or third-party programs/applications to collect and store data which could be used to assist in determining the patient's current situation, condition, and severity of an episode. The relevant data, relates to, but not limited to, the patient's mood, hours of sleep, medication consumption, caloric intake, menstruation, personal hygiene, classes, meetings, and other factors which are predetermined by the evaluation function 112, machine learning, statistics, artificial intelligence, dynamic feedback systems or the like.

In step 220, exploration function 116 explores the supplied data. The supplied data is dissected to create a set of data points. In some embodiments, the supplied data is divided into predetermined lengths. This allows the exploration function 116 to analyzes smaller sections of the supplied data, if it is likely that the original audio file is too large for the Neurological program 110 or the functions and functions to process. For example, if the supplied data is an audio file is divided into fifteen (15) second segments or segments of a predetermined length out of an original audio file that was sixty (60) seconds long. In some embodiments, where the supplied data is textual file, the textual file is divided into a predetermined quantity of pieces based on a predetermined maximum word count. The step 220 performed by exploration function 116 is further explained in FIG. 3 below.

In step 221, evaluation function 112 generates a confidence score as an additional product of the cognitive analysis. The confidence score measures the confidence the neural net has in its results. This score may be impacted by, but not limited to, the following: the semantic clarity of the speech, the extraction of the patient's words from background noise, poor annunciation, and unrecognized slang. A low confidence score may be interpreted by the Neurological program 110 or the functions as a sign of a low-quality recording or neurological symptoms such as an inability to speak clearly. A high confidence score may be interpreted by the Neurological program 110 or the functions as a sign of neurological symptoms such as extreme emotional expression or unusually clear diction. In some embodiments, the interpretation of the confidence score may be determined by, but not limited to, the following, the detection of background, non-patient sounds or noises, the inability to analyze the patient because of speed of speech, time of pausing, length of the pauses, slurring, incoherent statements, or other factors which would lead to less than accurate analyzes of the spoken word. In some embodiments, where the supplied data is textual, the evaluation function 112 may produce a high confidence score based on the lack of transfer from the spoken work to textual situation that arises when the supplied data is audio. In additional embodiments, evaluation function 112 performs or applies a cognitive computing assessment of a video.

In step 222, synthesis function 118, processes the supplied data and the relevant data to perform another calculation on the data created by the patient and the patient's device to further determine if the patient is experiencing an episode, and potentially the degree of the episode. Once the supplied data is explored as explained in FIG. 3, the synthesis function 118 uses the supplied data and the relevant data and performs another calculation on the likelihood of the patient having an episode as shown and further described in FIG. 4

In step 224, evaluation function 112 calculates an episode score based on the collected data from the exploration function 116 and the synthesis function 118 analyses of the supplied data and the relevant data. This episode score is used to determine if the patient is likely to be experiencing an episode based on their physical and verbal traits at the time of inputting data. The evaluation function 112 uses the data calculated from the exploration function 116 and the synthesis function 118 to calculate the episode score. This includes, but is not limited to the confidence scores of the exploration function 116, the vector calculations, the silhouette score, the clustering calculations, the analyses of the relevant data, or other calculations performed by the synthesis function 118. The evaluation function 112 gathers a plurality of the calculations and scores and generates an episode score. In some embodiments, the calculated data from the exploration function 116 and the synthesis function 118 have a predetermined hierarchy or importance rating relative to the rest of the calculated data.

In another embodiment, the score is calculated based on Bayes Theorem or another Baysian method which predicts the probability that an episode is happening. The method calculates the score based on the emotional state of the user based on various emotions, such as, but not limited to anger, happiness, sad, natural, fear, or various other emotions. In some embodiments, classifiers may be used to recognize emotion, such as, but not limited to Naïve Bayes classifiers, K-NN (K-nearest neighbors) classifiers, Gaussian Mixture Models (GMM) classifiers, or the like. The Bayes Theorem, in one embodiment, may be predisposed to ambiguous cases and produces a medium score. In additional embodiments, the Bayes Theorem, may be trained in multiple categories, and produces a score that is more patient specific. Bayes theorem estimates the odds of one event happening given the odds of other related events.

In some embodiments, the episode score is calculated based on previously stored data to establish when the patient is not having an episode, having a minor episode, having an extreme episode, or various stages between which are used to adjust the episode score.

In some embodiments, the episode score may be based on only the patient supplied data of this instance. In additional embodiments, the episode score may be based on, but not limited to, the calculated data and the other patient episode scores and associated data, a generic episode score and the associated data, or other prior collected or generated data.

In decision 226, evaluation function 112 determines if the episode score is outside the predetermined value(s). The threshold value(s) are value(s) that are used to determine if the patient is exhibiting characteristics or having an episode based on their condition. In some embodiments, the episode score is compared to a general episode score created based on previously collected data associated with various patients with similar or like conditions, or a calculated average range of a model patient. In some embodiments, the episode score is compared to previous episode scores of the specific patient. In the embodiment, where the episode score is based on the specific patient's previous episode scores, the threshold value is continuously modifying based on the additional data gathered. If evaluation function 112 determines that the episode score is outside the predetermined value range (NO branch, proceed to step 208) and evaluation function 112 alerts the patient. If evaluation function 112 determines that the episode score is within the predetermined value range (YES branch, proceed to step 226) evaluation function 112 provides adjusted episode score to patient.

In step 228, evaluation function 112 provides the adjusted episode score to the patient. This assists the patient in determining how they are doing compared to their previous entries, or an average score based on their condition. This is valuable for the patient because it informs them of how they are doing compared to before, to best allow them to personally make modifications to their mental, emotional, physical, or environmental state to return them to a state of tranquility or awareness. In some embodiments the episode score is based on a predetermined 1-10 or 1-100 scale which is related to the episode score produced in step 224. In some embodiments, the episode score, based on the value is displayed in various colors (e.g. green for good, yellow for warning, red or problem), sizes (larger for more severe values), paired with sounds and other visual or audible cues to alert the patient. In some embodiments, this score is also provided to preapproved personnel in additional to the patient.

In step 230, evaluation function 112 requests additional information from the patient. The evaluation function 112 requests the patient to provide additional information to assist in determining how they are feeling to further verify the accuracy of the data. In some embodiments where the patient receives a score of predetermined value, the evaluation function 112 provides the patient with follow up questions to determine, for example, how they are feeling, if they feel they are having an episode, how their mood is, their feelings, or the like, to better determine what is causing the average or positive scores. The questions' appearance may be determined based on the patient's score, where a score closer to the average will initial a larger set of questions, comments, or advice than a score that is at the higher end of their scale.

In step 232, evaluation function 112 stores the data. The evaluation function 112 stores the data with either the patient's data, the pool of patient's data, or a combination of both. This data is stored to assist in creating the average and characteristics associated with the various conditions to further create real life signs and signals for when episodes occur. When the data is stored, the patient and the patient pool averages and factors are adjusted and further refined. In some embodiments, this happens automatically. In additional embodiments, a provider needs to approve the storing of the data, as there may be instances where false positives are shown which would negatively affect the calculated data. In some embodiments, predetermined sections of the data collected and received by the Neurological program 110 or the functions stored.

Figure 3:
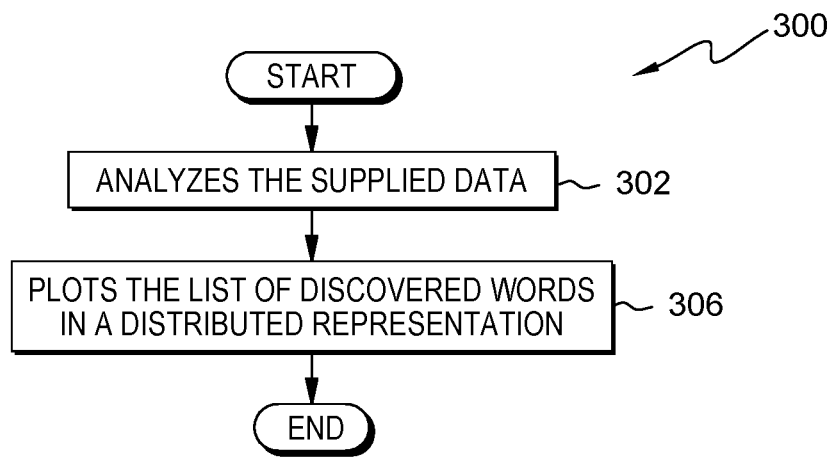
FIG. 3 depicts a flowchart of the operational steps taken by neurological program to explore the gathered with the assistance of a computing device within the computing environment of FIG. 1, in accordance with an embodiment of the present invention.

FIG. 3 shows flowchart 300 depicting a method according to the present invention. The method(s) and associated process(es) are now discussed, over the course of the following paragraphs, with extensive reference to FIG. 3, in accordance with one embodiment of the present invention.

In step 302, exploration function 116 analyzes the supplied data. Exploration function 116 uses a form of cognitive computing to analyze the supplied data to gather a list of discovered words which were recorded in the supplied data or generate other observations. In one embodiment, the cognitive computing is a neural net, which may be, but not limited to, deep neural networks, recurrent neural networks, transcript neural net, sentiment neural net, semantic neural net, or other forms of cognitive computing such as artificial intelligence or other advanced computing methods to analyze, calculate, and determine spoken words from the supplied data. In some embodiments, a tagging architecture or similar word detection algorithms may be employed to analyze the supplied data, such as, but not limited to, Bayes Theorem or Bayesian Methods. The detection algorithm(s) analyzes the emotional state of the user based on various emotions, such as, but not limited to anger, happiness, sad, natural, fear, or various other emotions. In some embodiments, classifiers may be used to recognize emotion, such as, but not limited to Naïve Bayes classifiers, K-NN (K-nearest neighbors) classifiers, Gaussian Mixture Models (GMM) classifiers, or the like. This analyzes of the supplied data may be, but not limited to the following: speech recognition, semantic analysis, sentiment analysis, and the like. In one embodiment, the exploration function 116 has the ability to distinguish between background noise and the patient's voice based on predetermined data, which allows the exploration function 116 to analyze data related only to the patient. In some embodiments, the separation of the patient's data and the background noise is performed in later steps. In one embodiment, the exploration function 116 is able to distinguish between a first speaker, a second speaker, and the background noise to consolidate the information gathered from the supplied data.

In step 304, exploration function 116 plots the list of discovered words in a Distributed Representation of language created through Word Embedding techniques. Exploration function 116 calculates the relationship between the list of discovered words plotted. Exploration function 116 takes the list of discovered words and plots them in predetermined locations based on a predetermined plot or map, which represents the relationships every word in a given language. The location of where the words are plotted is predetermined based on the type of plot which is used. The type of plot may be based on the type of process performed by the exploration function 116, the language, or various other factors.

Figure 4:
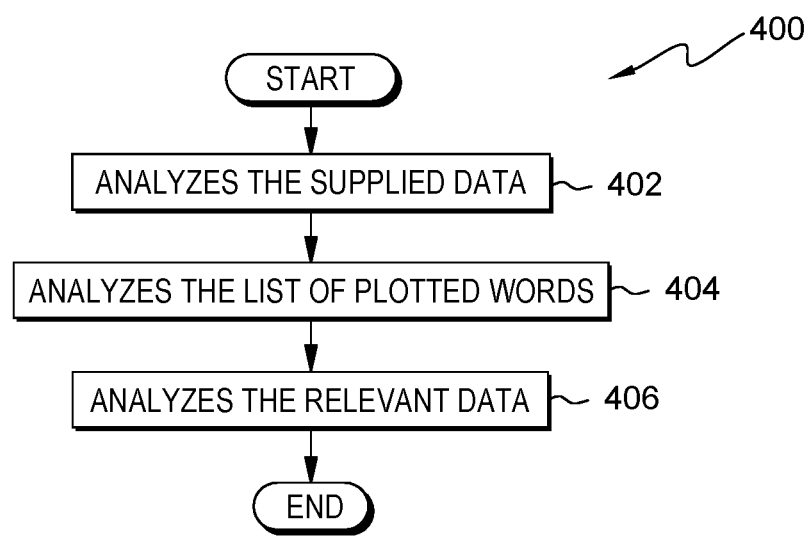
FIG. 4 depicts a flowchart of the operational steps taken by neurological program to synthesizes the data explored with the assistance of a computing device within the computing environment of FIG. 1, in accordance with an embodiment of the present invention.

FIG. 4 shows flowchart 400 depicting a method according to the present invention. The method(s) and associated process(es) are now discussed, over the course of the following paragraphs, with extensive reference to FIG. 4, in accordance with one embodiment of the present invention.

In step 402, the synthesis function 118 analyzes the supplied data and further analyzes the data returned from the exploration function. The synthesis function 118 processes the supplied data in the audio, textual, or video form and analyses the various features of the supplied data to gather additional information which was not gathered by the exploration step. For example, by analyzing data from the previous steps, the synthesis function 118 analyzes patterns of pauses, the articulation of the patient's speech, the speed of speech (e.g. how many words per minute, or the like), slurring, volume of the words, the presence of inappropriate language, repetition of words, or other characteristics of the spoken words. In embodiments, where a video is provided, the synthesis function 118 analyzes the movement of the video, the various items or facial characteristics shown in the video in additional to any features or characteristics of the supplied audio.

In step 404, the synthesis function 118 analyzes the plotted words in the distributed representation. Synthesis function 118 takes the plotted words by the exploration function 116 and calculates, a number of clusters, the density of the clusters, the distance between at least two clusters, the distance between at least two of the plotted words, various of types of special information related to the plotted words and the formed clusters, and other analyses.

To form the clusters of the plotted words, synthesis function 118 performs a clustering vector analysis. The clustering vector analysis calculates the distance between two or more words, identifies central points such that the distance from each word to a point is minimized, and groups the words based on which central point they're closest to. These groups contain words that are semantically related. In one embodiment, the exploration function 116 performs similar measurements (some involving clusters, some simply performing measurements of distance and patterns of distance) between a predetermined set of words in the list of discovered words, which are plotted. In additional embodiments, the exploration function 116 performs similar measurements (some involving clusters, some simply performing measurements of distance and patterns of distance) between substantially every word of the list of discovered words.

The vectoring is a pre-trained vector space—also known as a distributed representation—of the English language (but not limited to all other languages), wherein the vector analysis has predetermined distributed representation of the languages known words, wherein the relationships between the known words is predetermined. In some embodiments, the known words are gathered from additional sources such as dictionaries or various word libraries.

In some embodiments, a clustering analysis is performed on the plotted words. The clustering analysis is performing the task of grouping the discovered words in such a way that words of similar topics, functions, or features form clusters and are more similar to each other than to those in other clusters. The clustering analysis may be performed by various algorithms or mathematical calculation.

In additional embodiments, a semantic vector space in a first language may be used to find translations of words from the first language to a second language using a translation matrix between the first language and the second language. This translation matrix may, in example embodiments, provide a linear or affine transform from the semantic vector space of the first language to semantic vector space of the second language. In yet another embodiment, a semantic vector representation of a corpus of words of a first language may be generated in the semantic vector space of that first language.

In additional embodiments, a language-integrated query (LINQ) operator can be generated and executed with particular parameters in order to effect a change of basis for a set of vectors. The set of vectors can be related to a digital signal processing (DSP) environment in which the set of vectors can be any suitable vector corresponding to discrete time signals. Specifically, LINQ operators can be executed with parameters in order to change the set of vectors from one basis to another basis. In other words, LINQ operators can perform transforms for vector data rather than complex computations or algorithms.

In some embodiments, a silhouette value is calculated to determine the cohesion of a cluster compared to the disorganization, spread, or messiness of the clusters.

In step 406, the synthesis function 118 analyzes the relevant data. The synthesis function 118 process the relevant data to gather information from the patient's device. This could include, but not limited to, the accelerometer, the gyroscope, the global positioning system data, heart rate, caloric intake, and other data which could be collected by the patient's device or other applications or software that could be used to assist in determining if the patient is experiencing an episode.

Figure 5:
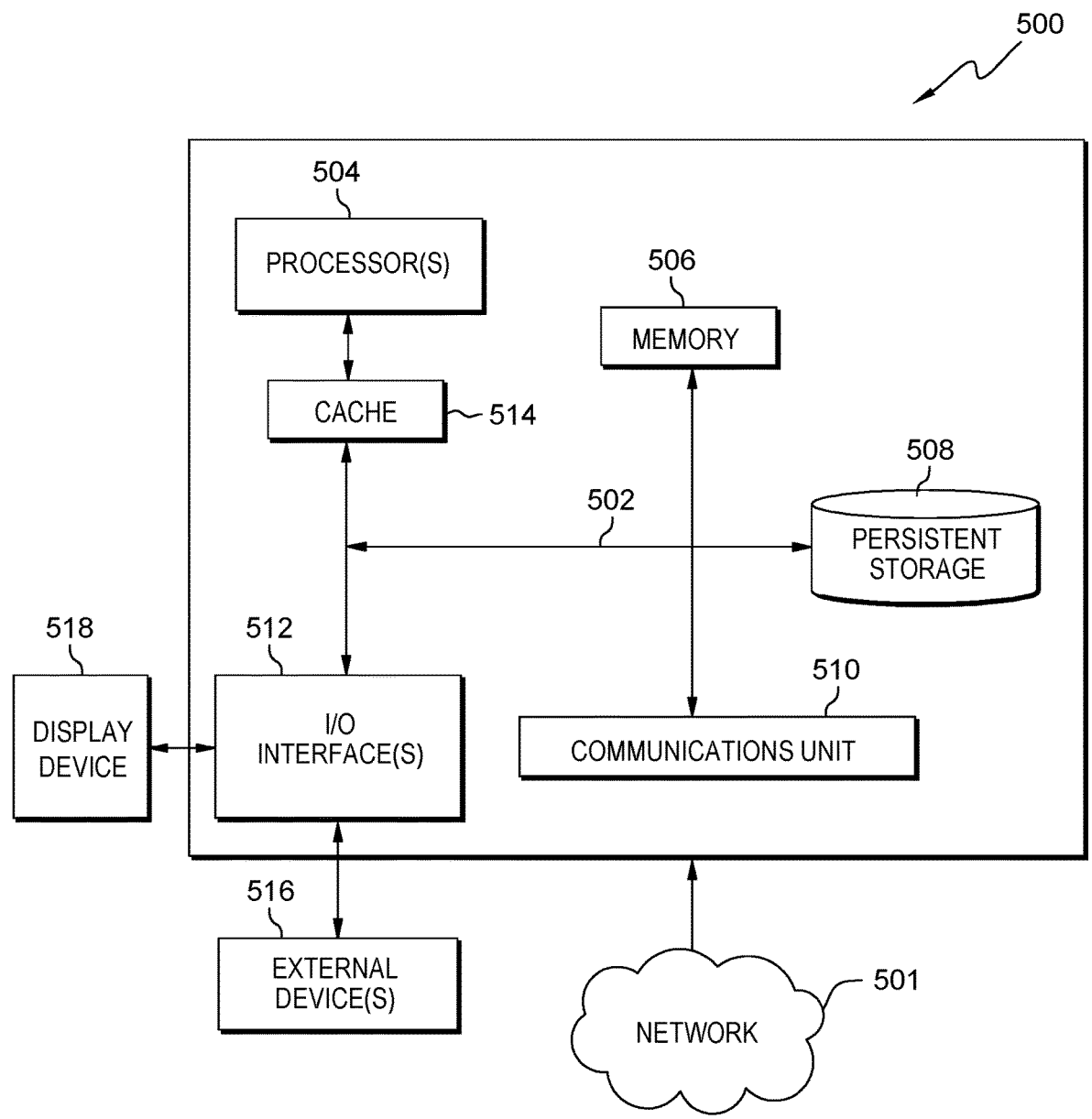
FIG. 5 depicts a block diagram depicting the internal and external components of the server of FIG. 1, in accordance with one embodiment of the present invention.

FIG. 5 depicts a block diagram 500 of components of a computing device (e.g. patient computing device 104, personnel computing device 106, or server 108), in accordance with an illustrative embodiment of the present invention. It should be appreciated that FIG. 1 provides only an illustration of one implementation and does not imply any limitations with regard to the environments in which different embodiments may be implemented. Many modifications to the depicted environment may be made. It should be appreciated FIG. 1 provides only an illustration of one implementation and does not imply any limitations with regard to the environments in which different embodiments may be implemented.

Computing environment 500 is, in many respects, representative of the various computer subsystem(s) in the present invention. Accordingly, several portions of computing environment 500 will now be discussed in the following paragraphs.

Computing device 500 includes communications fabric 502, which provides communications between computer processor(s) 504, memory 506, persistent storage 508, communications unit 510, and input/output (I/O) interface(s) 512. Communications fabric 502 can be implemented with any architecture designed for passing data and/or control information between processors (such as microprocessors, communications and network processors, etc.), system memory, peripheral devices, and any additional hardware components within a system. For example, communications fabric 502 can be implemented with one or more buses.

Computing device 500 is capable of communicating with other computer subsystems via network 501. Network 501 can be, for example, a local area network (LAN), a wide area network (WAN) such as the Internet, or a combination of the two, and can include wired, wireless, or fiber optic connections. In general, network 501 can be any combination of connections and protocols that will support communications between computing device 500 and other computing devices.

Memory 506 and persistent storage 508 are computer-readable storage media. In one embodiment, memory 506 includes random access memory (RAM) and cache memory 514. In general, memory 506 can include any suitable volatile or non-volatile computer-readable storage media.

Memory 506 is stored for execution by one or more of the respective computer processors 504 of computing device 500 via one or more memories of memory 506 of computing device 500. In the depicted embodiment, persistent storage 508 includes a magnetic hard disk drive. Alternatively, or in addition to a magnetic hard disk drive, persistent storage 508 can include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 508 may also be removable. For example, a removable hard drive may be used for persistent storage 508. Other examples include optical and magnetic disks, thumb drives, and smart cards that are inserted into a drive for transfer onto another computer-readable storage medium that is also part of persistent storage 508.

Communications unit 510, in the examples, provides for communications with other data processing systems or devices, including computing device 500. In the examples, communications unit 510 includes one or more network interface cards. Communications unit 510 may provide communications through the use of either or both physical and wireless communications links.

I/O interface(s) 512 allows for input and output of data with other devices that may be connected to computing device 500. For example, I/O interface 512 may provide a connection to external devices 516 such as a keyboard, keypad, camera, a touch screen, and/or some other suitable input device. External devices 516 can also include portable computer-readable storage media such as, for example, thumb drives, portable optical or magnetic disks, and memory cards. Software and data used to practice embodiments of the present invention, e.g., Neurological program 110, evaluation function 112, exploration function 116, and/or synthesis function 118 can be stored on such portable computer-readable storage media and can be loaded onto persistent storage 508 of computing device 500 via I/O interface(s) 512 of computing device 500. Software and data used to practice embodiments of the present invention, e.g., Neurological program 110, evaluation function 112, exploration function 116, and/or synthesis function 118 can be stored on such portable computer-readable storage media and can be loaded onto persistent storage 508 of computing device 500 via I/O interface(s) 512 of computing device 500. I/O interface(s) 512 also connect to a display 518.

Display 518 provides a mechanism to display data to a patient and may be, for example, a computer monitor.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the patient's computer, partly on the patient's computer, as a stand-alone software package, partly on the patient's computer and partly on a remote computer or entirely on the remote computer or server. In the latter scenario, the remote computer may be connected to the patient's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein that are believed as maybe being new, this understanding, as indicated by use of the term "present invention," is tentative and provisional and subject to change over the course of patent prosecution as relevant information is developed and as the claims are potentially amended.

What is claimed is:

1. A method for identifying, measuring the severity of, and providing care for an impairment in a patient's cognitive or emotional condition, the method comprising:

recording, by one or more processors, a first set of audio data, wherein the first set of audio data is requested at a predetermined time;

converting, by one or more processors, the first set of audio data to a second set of textual data, wherein the second set of textual data represents the textual representation of the words of the first set of audio data;

analyzing, by one or more processors, the first set of audio data based on a first set of audible characteristics;

analyzing, by one or more processors, the second set of textual data based on sentiment and semantic characteristics;

calculating, by one or more processors, a confidence score, wherein the confidence score is related to the clarity of the audio and the accuracy of the translation of the first set of audio data into the second set of textual data;

establishing, by one or more processors, a relationship between the first set of audio data and the second set of textual data, wherein the relationship represents a correlation between the audible characteristics of the first set of audio data and the sentiment and semantic characteristics of the second set of textual data;

comparing, by one or more processors, the relationship between the first set of audio data and the second set of textual data to a baseline value; and calculating, by one or more processors, a rating based on the compared relationship and the confidence score.

2. The method of claim 1, further comprising, prompting, by one or more processors, the patient to input the first set of audio data.

3. The method of claim 1, wherein, the analyzing a first portion of the first set of audio data, further comprises, calculating, by one or more processors, a distribution representation of the plotted the first portion of the first set of audio data.

4. The method of claim 1, wherein, a pre-trained neural net, analyzes the first portion of the first set of audio data using a semantic analysis, a speech to text analysis, a sentiment analysis, or a combination of relative to a set of pre-trained conditions.

5. The method of claim 3, wherein, the analyzing the first portion of the first set of data, further comprises, calculating, by one or more processors, a silhouette score based on a quantity of clusters, wherein the quantity of clusters are based on the plotted first portion of the first set of data in the distributed representation of at least one language.

6. The method of claim 1, wherein, the step of calculating the baseline value, further comprises, determining, by one or more processors, based on previously-collected user data, the likelihood and severity of a pathology using a Baysian statistical technique.

7. A computer program product for identifying, measuring the severity of, and providing care for an impairment in a patient's cognitive or emotional condition, the computer program product comprising:

one or more computer readable storage media and program instructions stored on the one or more computer readable storage media, the program instructions comprising:

program instructions to request the patient to input audio data at a predetermined time or location;

program instructions to record audio data from the patient;

program instructions to convert the audio data to textual data;

program instructions to analyze the audio data based on audible characteristics;

program instructions to analyze the textual data based on sentiment and semantic characteristics;

program instructions to calculate a confidence score, wherein the confidence score is related to the accuracy of the analysis of the sentiment and semantic characteristics of the textual data;

program instructions to establish a relationship between the audio data and the textual data, wherein the relationship represents a correlation between the audible characteristics of the audio data and the sentiment and semantic characteristics of the textual data;

program instructions to plot the relationship between the audio data and the textual data;

program instructions to compare, the relationship between the audio data and the textual data to a baseline value; and program instructions to calculate a rating based on the compared relationship.

8. The computer program product of claim 7, further comprising, computer instructions to prompt the patient to input the audio data.

9. The computer program product of claim 7, wherein the program instructions to analyze the audio data, further comprises, program instructions to calculate a distribution representation of the plotted audio data.

10. The computer program product of claim 7, wherein, a pre-trained neural net, analyzes the audio data using a semantic analysis, a speech to text analysis, a sentiment analysis, or a combination of relative to a set of pre-trained conditions.

11. The computer program product of claim 10, wherein, the computer instruction to analyze audio data, further comprises, program instructions to calculate a silhouette score based on a quantity of clusters, wherein the quantity of clusters are based on the plotted first portion of audio data in the distributed representation of at least one language.

12. The computer program product of claim 7, further comprising, computer instructions to provide an alert to predetermined computing devices, wherein the rating value is within a predetermined range.

13. A computer system for protecting a resource, the computer system comprising:

one or more computer processors, one or more computer readable storage media, and program instructions stored on the one or more computer readable storage media for execution by, at least one of the one or more processors, the program instructions comprising:

program instructions to prompt a request to a patient requesting audio data at a predetermined time or location;

program instructions to receive the audio data;

program instructions to record the audio data;

program instructions to convert the audio data to textual data;

program instructions to collect a set of recorded data, wherein the set of recorded data is collected from a patient's computing device;

program instructions to analyze the audio data based on audible characteristics;

program instructions to analyze the textual data based on sentiment and semantic characteristics;

program instructions to calculate a confidence score, wherein the confidence score is related to the clarity of the patient's speech and accuracy of the analysis of the sentiment and semantic characteristics of the textual data;

program instructions to plot the audio data in a predetermined graphical representation of at least one language, wherein the plot represents a correlation between each of the spoken words;

program instructions to establish the a relationship between the audio data and the textual data, wherein the relationship represents a correlation between the audible characteristics of the audio data and the sentiment and semantic characteristics of the textual data;

program instructions to compare the relationship between the audio data and the textual data to a baseline value; and program instructions to calculate a rating based on the compared relationship and the set of record data.

14. The computer system of claim 13, wherein the program instructions to analyze the audio data, further comprises, program instructions to calculate the distribution representation of the plotted audio data.

15. The computer system of claim 13, wherein, a pre-trained neural net, analyzes the audio data using a semantic analysis, a speech to text analysis, a sentiment analysis, or a combination of relative to a set of pre-trained conditions.

16. The computer program product of claim 7, wherein, the analyzed the audio data with a pre-trained neural net, analyzes a predetermined quantity of audible features.

17. The computer system product of claim 13, wherein, the computer instruction to calculate the baseline value, further comprises, computer instructions to determine based on previously-collected user data the likelihood and severity of a pathology using a Bayesian technique.

18. The computer system of claim 13, further comprising, computer instructions to provide an alert to predetermined computing devices, wherein a calculated value is within a predetermined range.

19. The method of claim 1, further comprising, training, by one or more processors, a module with the analyzed first set of audio data, the processed second set of textual data, and a third set of recorded data, wherein the trained module forms the baseline value.

20. The method of claim 1, wherein the comparison of the relationship between the first set of audio data and the second set of textual data is represented as a deviation from the baseline value.

21. The method of claim 1, further comprising, collecting, by one or more processors a set of record data, collected from a patient's computing device.

22. The method of claim 21, further comprising, analyzing, by one or more processors the set of record data and applying this analyzed set of recorded data in the calculation of the rating.

* * * * *